United States Patent [19]

Klepacki

[11] 4,445,861

[45] May 1, 1984

[54] DENTURE SUPPORT SYSTEM AND METHOD

[76] Inventor: Michael A. Klepacki, 5403 Ellsworth, Dallas, Tex. 75206

[21] Appl. No.: 440,005

[22] Filed: Nov. 8, 1982

[51] Int. Cl.³ .............................................. A61C 13/22
[52] U.S. Cl. ........................................ 433/181; 433/9
[58] Field of Search ............... 433/181, 182, 180, 172, 433/183, 9, 8

[56] References Cited

U.S. PATENT DOCUMENTS

| | | | |
|---|---|---|---|
| 1,183,396 | 5/1916 | Morgan | 433/183 |
| 1,218,033 | 4/1917 | Yirikian | 433/181 |
| 1,340,089 | 5/1920 | Stone | 433/181 |
| 1,698,259 | 10/1929 | Craig | 433/181 |
| 1,705,504 | 7/1929 | Sorensen | 433/181 |
| 1,721,443 | 6/1929 | Gregg | 433/181 |
| 2,016,511 | 9/1935 | Oppenheimer | 433/181 |
| 2,151,723 | 3/1939 | Trinkle | 433/172 |
| 2,889,625 | 6/1959 | Saffir | 433/180 |
| 3,043,007 | 7/1962 | Wallshein | 433/8 |
| 3,057,068 | 10/1962 | Morandi | 433/172 |
| 4,337,037 | 6/1982 | Kurz | 433/8 |
| 4,360,342 | 11/1982 | Salvo | 433/180 |

*Primary Examiner*—John J. Wilson
*Attorney, Agent, or Firm*—Hubbard, Thurman, Turner & Tucker

[57] ABSTRACT

A partial denture for the mandibular region is at least partially supported by brackets bonded to the lingual surfaces of one or more of the mandibular anterior teeth. The support brackets are mounted on the lingual tooth surfaces which are prepared by grinding a small horizontal ledge and a generally planar support surface for bonding the brackets to the tooth surfaces for transferring forces in a generally vertical direction directly to the teeth and along a line relatively close to the longitudinal vertical axis of the tooth. The support brackets are provided with a U shaped recess forming spaced apart upstanding legs to maximize the distribution of supporting loads between the bracket and the tooth.

6 Claims, 7 Drawing Figures

DENTURE SUPPORT SYSTEM AND METHOD

BACKGROUND OF THE INVENTION

1. Field of the Invention

The present invention pertains to a method for supporting a partial denture and an improved support bracket or rest for the denture frame.

2. Background

In the art of prosthodontics the replacement of missing teeth in the mandibular region of the mouth has presented several longstanding problems. Partial dentures for the lower teeth cannot take advantage of structure other than the remaining teeth themselves or permanent crowns for supporting the denture frame. As compared with the maxillary region there is no bony structure, such as the hard palate, to which the mastication forces can be transferred. Moreover, if the mandibular anterior teeth are the only ones which are sound these teeth do not have sufficient enamel thickness to provide for the formation of a suitable recess or rest seat in which a corresponding portion of the denture frame may be fitted.

Since the transfer of mastication forces and forcible contact of the denture with the gingiva should be avoided, and the mandibular anterior teeth are in many cases the only remaining sound tooth structures available for supporting the denture frame, the prior art practice has been to provide rests where enamel thickness is marginal or placement of rests in positions wherein the forces exerted thereon tend to rotate or deflect the tooth. Alternative techniques have included crowning the mandibular anterior teeth so that permanent rests can be provided, or the anterior teeth are removed so that a full denture plate can be inserted. From an economic and health standpoint none of these techniques is as desirable as the provision of a suitably supported partial denture. For example, in regard to full mandibular dental prostheses they are almost always more difficult to retain than a well made partial denture. Mobility of partial or full dentures tends to accelerate the amount of bone loss which can greatly decrease the time span during which the patient can wear a dental prosthesis successfully. Accordingly, prior to the development of the present invention the provision of partial dentures for the mandibular region has been fraught with several problems, depending on the tooth structures available for supporting the denture frame, and particularly in instances where only the mandibular anterior teeth remain relatively sound as structures for anchoring or supporting a portion of the denture plate.

SUMMARY OF THE INVENTION

The present invention provides a partial dental prosthesis particularly adapted for providing artificial mandibular teeth, which prosthesis is supported in an improved manner by a unique support system which is provided by an improved procedure wherein permanent rests are supported on the lingual surfaces of the mandibular anterior teeth, and which rests are preferably spaced apart and supported on the mandibular canine teeth.

In accordance with one aspect of the present invention there is provided an improved denture support bracket or rest structure which may be applied to the lingual surface of the mandibular anterior teeth to provide a support for a denture frame in a such a way that denture supporting forces are transferred to the teeth with a minimum tendency to develop force couples which would tend to rotate the teeth. The improved support bracket is also adapted to be cooperable with a supporting ledge formed on the tooth surface and is of a configuration which, when adhered to a prepared surface on the tooth, distributes forces uniformly over a relatively large area. The improved denture support bracket is also adapted to provide for cooperable rest portions to be formed on the denture support frame without interfering with the support structure of the bracket itself. The denture support bracket is further configured to provide for easy cleaning of the tooth in the area of the bracket, including the bracket itself, and to minimize irritation of the tongue when the denture is removed.

In accordance with another aspect of the present invention there is provided an improved arrangement of a partial denture which is supported by prefabricated support brackets or rests secured to the lingual surfaces of the mandibular anterior teeth thereby eliminating the need for incisal rests and wherein the mastication forces applied to the denture are transferred to sound tooth structures and at positions which minimize the effect of reaction forces on the tooth structure.

In accordance with a further aspect of the present invention there is provided a method of supporting a mandibular partial denture utilizing the anterior teeth and wherein the denture is supported by rests on the lingual surface of the teeth where enamel thickness is insufficient and the slope of the surface is normally not satifactory to prepare a rest seat of suitable form in accordance with prior art practices.

In accordance with yet another aspect of the present invention there is provided an improved method of preparation and formation of a supporting surface on one or more of the mandibular anterior teeth for supporting an improved support bracket or rest which is bonded to the surface of the tooth. Depending on which teeth remain sound it is preferred that the improved process of the present invention be carried out using the inventive support bracket on the lingual surfaces of the mandibular canines or stomach teeth. The spacing of these teeth provide a suitable horizontal spread between supports to enhance the stability of the prosthesis.

Those skilled in the art will further appreciate the abovementioned aspects of the present invention as well as other superior features thereof upon reading the detailed description which follows in conjunction with the drawings.

BRIEF DESCRIPTION THE DRAWINGS

DESCRIPTION OF THE PREFERRED EMBODIMENTS

Figure 1:
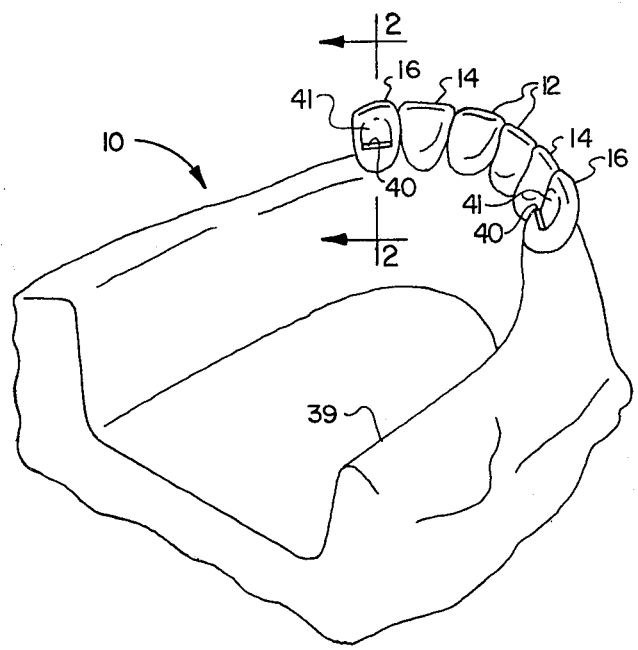
FIG. 1 is a perspective view of the mandibular region of the human mouth showing a typical arrangement of permanent teeth commonly remaining in a patient of denture age.

In the description which follows like parts are indicated throughout the specification and drawings with the same reference numerals, respectively. The drawings are not necessarily to scale and certain elements illustrated may be exaggerated in scale in order to show the inventive features and in the interest of clarity and conciseness.

Referring to FIG. 1 there is illustrated a perspective view of the mandibular region of the human mouth, generally designated by the numeral 10. The representation of the mouth area 10 includes the mandibular anterior teeth including the central incisors 12, the lateral incisors 14 and the canines or stomach teeth 16. The arrangement of the mandibular region illustrated is for illustrative purposes only but is indicative of the condition of a patient's mouth of denture age and wherein the teeth which are still sound are basically in the anterior region, which region shows a somewhat lower caries incidence than the teeth of the posterior region.

In an instance where the first premolars remain sound and both second or third molars are sound it is sometimes possible to adequately support a partial denture prosthesis by cutting sockets or recesses into these teeth to receive cast rests or support surfaces comprising part of the denture frame. Such structure together with conventional clasps may be adequate to properly support a mandibular prosthesis. However, in the instance illustrated and in situations where the premolars remain in place but are considered structurally unsound there is inadequate structure present for supporting the denture frame in the anterior region. In the prior art, in instances such as discussed above, it has been conventional to remove portions of the canines or the lateral incisors or even the central incisors and replace these teeth with crowns in which suitable rests or recessed surfaces may be provided for receiving the support arms of a denture support frame. However, in accordance with the present invention an improved method of supporting a denture frame is provided including a method of preparing a surface on mandibular anterior teeth such as the canines 16 and, which invention further includes an improved support bracket for supporting a partial denture.

Typically, the mandibular canines and incisors do not have enough enamel to permit the formation of a socketlike recess for a cast support arm of a denture frame so that the frame is not displaced into forcible engagement with the gingiva. However, the present invention contemplates the provision of an improved denture support bracket providing a rest which is formed on the lingual surface of one or more teeth of the mandibular anterior region. In accordance with a preferred embodiment of the present invention the mandibular canine teeth are each adapted to receive in supportive relationship a support bracket which provides a support or rest for a portion of a denture frame and which is disposed on a lingual surface of each of the canines.

Figure 7:
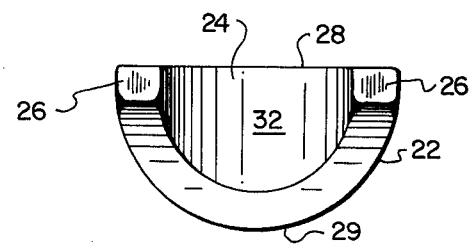
FIG. 7 is a top plan view of the support bracket.
Figure 5:
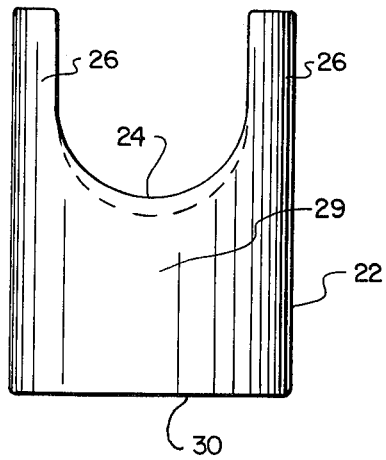
FIG. 5 is a front elevation of the support bracket of the present invention.
Figure 6:
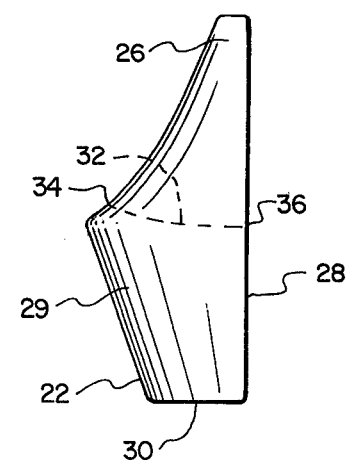
FIG. 6 is a side elevation of the support bracket shown in FIG. 5.

Referring to FIGS. 5 through 7, the support bracket of the present invention is characterized by a small blocklike element, generally designated by the numeral 22. The bracket 22 includes a somewhat U shaped recess 24 defined in part by a pair of spaced apart upstanding legs 26 which normally, in application of the bracket, extend vertically beyond the point of transfer of forces from the denture frame to the bracket. The backside of the bracket 22 is formed by a planar surface 28 which, in accordance with the present invention, is bonded to a surface of a tooth as prepared in a preferred manner to be described herein. The bracket 22 is also characterized by a curved front surface 29, and a planar bottom edge 30. The recess 24 is delimited by a curved surface 32 which intersects the distal portion of the surface 29 at a point 34 which is further from the edge 30 than the point of intersection of the surface 32 with the surface 28, which point of intersection is designated by the numeral 36 in FIG. 6. The shape of the bracket 22 as provided by the curved front surface 29 is particularly advantageous when placed on either the lingual or labial surfaces of the teeth to minimize irritation of the tongue or other tissues of the mouth. Moreover, the provision of the recess or socket 24 and the opposed legs 26 renders a superior supporting structure for transferring forces to the tooth on which the bracket is mounted and for distributing the forces over a greater surface area. The length of the legs 26 measured from point 36 is normally at least equal to the length of the surface 28 from point 32 to the edge 30. Finally, the provision of the generally planar transverse bottom edge 30 provides for supporting the bracket on a cooperating support ledge formed in the enamel of the tooth. The bracket 22 is preferably cast or otherwise suitably formed of a material which may reside substantially permanently in the mouth. A typical material would be a cast or wrought stainless steel.

Referring again to FIGS. 1 and 2, the present invention contemplates mounting one of the brackets 22 on the lingual surface 38 of each of the mandibular canines. These teeth are preferred for supporting the bracket 22, when determined to be structurally sound, so that the horizontal spread between support points of the denture frame is maximized to prevent tilting or tipping of the frame. Additional brackets such as the bracket 22 can be added to the mandibular central and/or lateral incisors if necessary in place of the canines or in addition to providing such support brackets on the canines.

Figure 2:
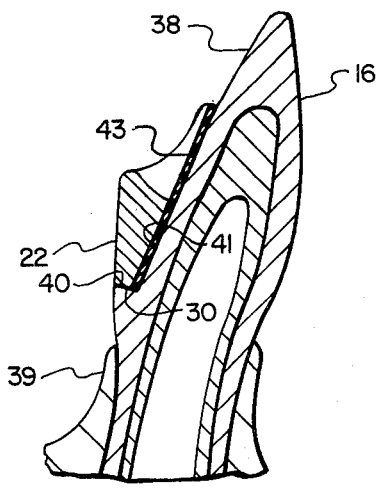
FIG. 2 is a section view taken along the line 2—2 of FIG. 1 showing the improved denture support bracket of the present invention in place on one of the mandibular canines.

In a typical example wherein a partial denture is provided to replace the mandibular posterior teeth the lingual surface of the canines 16 are modified by creating a substantially horizontal ledge, generally designated by the numeral 40 in FIGS. 1 and 2, in proximity to the gingiva 39 and preferably about 2.5 to 3.0 mm above the cemento-enamel junction on the lingual surface of the tooth. The ledge is anywhere from 0.50 to 0.75 mm wide and in no cases less than the width of the surface 28 of the bracket. The ledge 40 is preferably formed at a 90° angle with respect to the lingual surface 38 and a modified lingual surface 41 is formed, as shown in FIGS. 1 and 2, as a consequence of forming the ledge 40 and for the purpose of bonding the bracket to the tooth along the planar surface 28 of the bracket. A ledge formed in accordance with the abovementioned dimensions will preferably extend across approximately 75% of the mesio-distal width of the tooth. The bracket 22 is then bonded to the surface 41 and with the surfaces 30 and 40 contiguous with each other.

Accordingly, the bracket 22 is operable to transfer vertical loads resulting from masticatory forces and the like to the ledge 40 thereby reducing the loading on the bond between the bracket and the lingual surface, and reducing the tendency for the bracket to rotate itself and the tooth. By mounting the bracket 22 on the lingual surface of a tooth in the anterior region, such as the canines 16, the rest seat provided by the bracket for the denture framework is located in a low visability area and keeps the majority of the framework out of sight except for any retentive clasps which might be required on the labial surfaces. A still further advantage of the location and configuration of the bracket 22 relates to the cooperating support arm or rest portion of the denture framework which, when cast to provide a portion projecting into the recess 24, is of substantial mass and is less likely to break or be deformed. Moreover, the forces exerted on the bracket 22 and the tooth 16 by the denture framework are transferred to the tooth at a point which minimizes the tendency for the tooth to be deflected, that is, the forces are directed generally vertically downward and relatively close to the vertical longtiudinal axis of the tooth. The upward projecting legs 26 also distribute some of the loading to the tooth surface and reduce the tendency for the bracket to peel away from the bond interface.

Figure 4:
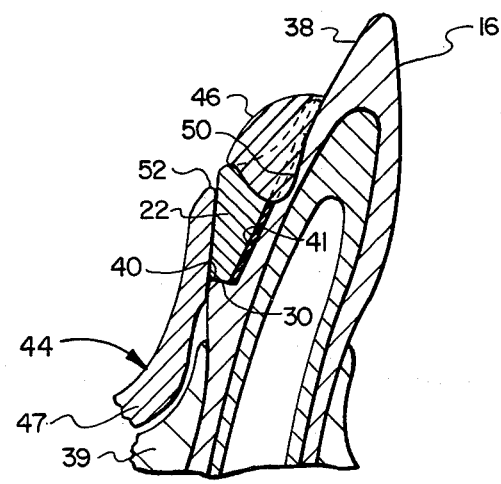
FIG. 4 is a section view taken along the line 4—4 of FIG. 3.
Figure 3:
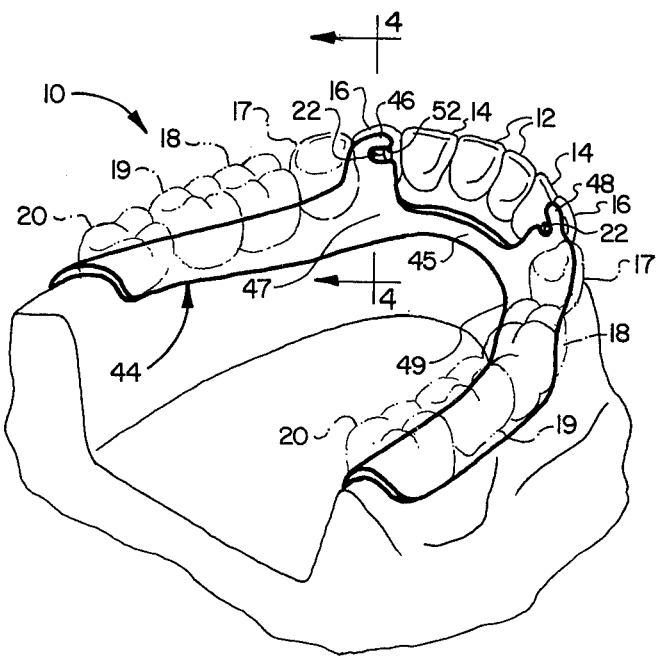
FIG. 3 is a perspective view similar to FIG. 1 showing a cast partial denture frame in place and supported by the arrangement of the present invention.

FIGS. 3 and 4 illustrate a denture framework, generally designated by the numeral 44, which has been fashioned to include opposed rest portions 46 and 48 engageable with brackets 22 on each of the mandibular canines 16. The denture frame 44 includes an arch bar 45 interconnecting opposed frame portions 47 and 49 which include the respective rest portions 46 and 48. The frame portions 47 and 49 extend toward the posterior region and are formed in a conventional manner to fit over the gingiva and be supportive of artificial mandibular posterior teeth designated by numerals 17 through 20, respectively. The frame 44 may be prepared in accordance with conventional denture casting and fabricating practices after the brackets 22 are applied to the selected mandibular anterior teeth. As shown in FIG. 4, after the bracket 22 is suitably mounted on the lingual surface 38, an additional depth of recess for receiving the rest portion 46 of the denture frame may be provided by grinding away additional enamel to form a recess 50 comprising a continuation of the recess 24 and complementary thereto. The rest portions 46 and 48 of the denture frame are preferably adapted to have a somewhat U shaped slot 52 formed therein to minimize the overall depth or thickness of the protrusion formed by the denture support frame and the bracket 22 which might otherwise interfere with or irritate the patient's tongue.

In preparing a partial denture in accordance with the present invention the mandibular anterior teeth are surveyed to determine if they are sound enough to support the brackets 22. In particular, the mandibular canines are preferred for supporting the brackets although, as mentioned previously, the lateral or central incisors may also be considered for receipt and support of the inventive bracket. Furthermore, depending on the integrity of one or more of the bicuspids, support for a denture plate can be enhanced by providing at least one of the rests to be formed by a bracket 22 disposed on an anterior tooth.

The procedure for preparing the mandibular anterior region for supporting a denture frame, after careful examination of the structural integrity of the teeth selected, preferably comprises preparing the surfaces 40 and 41 with a straight fissure burr being careful to form the surface or ledge 40 at about a 90° angle to the lingual surface of the tooth, and all the time being careful not to grind through the enamel into the dentin. The surface 41 is then etched with ascetic acid of conventional strength in the range of 35% to 50% for about one minute. The surface 41 is then rinsed and dried to a frosty white appearance. The brackets 22 are preferably applied to the surfaces 41 utilizing an adhesive such as a composite bonding resin of a type comparable to that which is manufactured under the trademark CONCISE by 3M Company, Minneapolis, Minn. The preparation comprises swabbing the etched area of the surface 41 with the liquid portion of the bonding agent and applying a layer of the paste portion of the bonding agent to the surface 28 of the bracket and adhering the bracket 22 to the surface 41 with the edges 30 and 40 contiguous with each other. Accordingly, when the bond cures a layer of bonding agent or adhesive 43 is formed between the bracket and the lingual surface of the tooth. The surface 28 may be knurled to increase the bonding strength between the adhesive and the bracket 22.

After allowing the adhesive 43 to cure the rest seat formed by the recess 24 in the bracket 22 is increased slightly in size by grinding the recess 50 with, for example, a No. 4 round burr. The formation of the recess or seat portion 50 not only increases the size of the seat area but provides for transferring some of the load of the denture frame support portions 46 or 48 directly to the tooth 16 instead of to the tooth through the bracket 22.

Following the mounting of one or more brackets 22, as required, excess composite or bonding material is cleaned away, the brackets polished and the areas treated resurveyed preparatory to fabricating the denture frame. Such framework is then fabricated in accordance with conventional denture casting practices and fitted to the patient.

The aforementioned inventive procedure and apparatus is believed to contribute to the goal of maintaining as many sound teeth in the mouth as possible and to use these teeth as points of stability and retention for a partial denture structure thereby by delaying or permanently avoiding the requirement to use a full denture. Although the bracket 22 is particularly useful in providing a permanent rest for a partial denture in the mandibular region the bracket may be used in conjunction with maxillary dentures as well as other procedures and apparatus for correcting or replacing dentition. Moreover, the bracket 22 can be mounted on a removable band or other structure which is adapted to be either permanently or temporarily supported in the mouth. However, the shape of the bracket 22 including the recess 24 and the leg portion 26 is particularly advantageous for permanent bonding to a prepared surface on a tooth.

Those skilled in the art will appreciate from the foregoing description that various substitutions and mocifications may be made to the method and articles of the present invention without departing from the scope and spirit of the invention as recited in the appended claims.

What I claim is:

1. A denture support bracket for use in supporting a denture frame or the like, said bracket comprising:
    a member having a generally planar backside forming a surface bondable to a mating surface formed on the exterior of a tooth, a generally horizontal bottom edge, and a recess for receiving and supporting a projecting portion of a denture support frame, said recess defining, in part, a pair of spaced apart upstanding legs of said bracket, each of said legs including a portion of said planar backside of said bracket.

2. The bracket set forth in claim 1 wherein:
said recess includes a base portion, and the length of said legs as measured from said base portion of said recess is at least equal to the distance from said base portion to said bottom edge.

3. The bracket set forth in claim 1 wherein:
said bracket includes a front side defined by a generally continuously curved surface extending from one longitudinal side edge of said bracket to the other longitudinal side edge and defining an irritation free lingual surface of said bracket.

4. A method for supporting a partial denture comprising the steps of:
providing two denture support brackets, each of said brackets having a generally horizontal support edge and a generally planar backside forming a surface for mounting said brackets on respective lingual tooth surfaces of two spaced apart mandibular anterior teeth, each of said brackets including means forming a recess for engaging spaced apart portions of a denture support frame, respectively;
forming a generally planar surface in the enamel of the lingual surface of each of two spaced apart anterior mandibular teeth and delimited by a generally horizontal support ledge on each of said teeth, respectively;
bonding said brackets to said teeth, respectively, with said recesses in said brackets opening in a generally upward direction, and with said support edges and said horizontal ledges engaged with each other, respectively, to transfer forces applied to said brackets to said respective teeth;
forming a denture support frame including said portions projecting into respective ones of said recesses in said brackets; and
supporting said support frame by said brackets to retain said denture securely to minimize the transmission of forces of mastication between said support frame and the gingiva.

5. The method set forth in claim 4 wherein:
said method includes the steps of forming a generally planar surface on each of the mandibular canine teeth and attaching one of said brackets to each of respective ones of said canine teeth, and said support frame is formed by casting a portion projecting into the recess of each of said support brackets.

6. A method for supporting a partial denture comprising the steps of:
providing at least one denture support bracket having a generally planar backside forming a surface for mounting said bracket on a lingual tooth surface in the anterior region, said bracket including means forming a recess for engaging a portion of a denture support frame;
forming a generally planar surface in the lingual surface of at least one anterior tooth;
attaching said one bracket to said one tooth with said recess in said bracket opening in a generally upward direction;
extending said recess in said one bracket by forming an adjacent recess portion in said lingual surface of said one tooth;
forming a denture support frame including casting said portion of said support frame to project into said recess in said bracket and to extend into said adjacent recess portion; and
supporting said support frame by said bracket to retain said denture securely to minimize the transmission of forces of mastication between said support frame and the gingiva.

* * * * *

UNITED STATES PATENT AND TRADEMARK OFFICE
CERTIFICATE OF CORRECTION

PATENT NO. : 4,445,861
DATED : May 1, 1984
INVENTOR(S) : Michael A. Klepacki

It is certified that error appears in the above-identified patent and that said Letters Patent is hereby corrected as shown below:

Column 6, line 53, change "mocifi-" to "modifi-"

Signed and Sealed this

Fifth Day of March 1985

[SEAL]

Attest:

DONALD J. QUIGG

Attesting Officer     Acting Commissioner of Patents and Trademarks